(12) United States Patent
Hazebrouck (10) Patent No.: US 7,125,423 B2
(45) Date of Patent: Oct. 24, 2006

(54) INTERCALARY PROSTHESIS, KIT AND METHOD

(75) Inventor: Stephen A. Hazebrouck, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 121 days.

(21) Appl. No.: 10/403,612

(22) Filed: Mar. 31, 2003

(65) Prior Publication Data

US 2004/0193268 A1 Sep. 30, 2004

(51) Int. Cl.
*A61F 2/28* (2006.01)

(52) U.S. Cl. .................. 623/16.11; 623/23.44; 623/23.47; 606/62

(58) Field of Classification Search ........... 623/16.11, 623/23.44, 23.47; 606/62, 63, 64
See application file for complete search history.

(56) References Cited

U.S. PATENT DOCUMENTS

| | | | | |
|---|---|---|---|---|
| 2,779,966 | A | * | 2/1957 | Torchia ................ 16/244 |
| 3,801,213 | A | * | 4/1974 | Eversole ............... 408/181 |
| 4,011,602 | A | | 3/1977 | Rybicki et al. |
| 4,016,874 | A | * | 4/1977 | Maffei et al. .......... 606/62 |
| 4,384,373 | A | | 5/1983 | Sivash |
| 4,467,794 | A | * | 8/1984 | Maffei et al. .......... 606/62 |
| 4,502,160 | A | | 3/1985 | Moore et al. |
| 4,634,444 | A | | 1/1987 | Noiles |
| 4,655,462 | A | | 4/1987 | Balsells |
| 4,676,797 | A | | 6/1987 | Anapliotis et al. |
| 4,787,907 | A | * | 11/1988 | Carignan .............. 623/23.44 |
| 4,826,144 | A | | 5/1989 | Balsells |
| 4,830,344 | A | | 5/1989 | Balsells |
| 4,876,781 | A | | 10/1989 | Balsells |
| 4,888,021 | A | | 12/1989 | Forte |
| 4,915,366 | A | | 4/1990 | Balsells |
| 4,934,666 | A | | 6/1990 | Balsells |
| 4,938,768 | A | | 7/1990 | Wu |

(Continued)

FOREIGN PATENT DOCUMENTS

DE 3535158 A 4/1987

(Continued)

OTHER PUBLICATIONS

Centerpulse Orthopedics, Inc. web site announcement *Centerpulse Orthopedics Announces Launch of Implant System for Revision and Trauma Patients*; http://www.centerpulseorthopedics.com/us/products/news/most_options_launch _12 _09. (4 pages); Dec. 9, 2002.

(Continued)

*Primary Examiner*—Corrine McDermott
*Assistant Examiner*—Thomas J Sweet (57) ABSTRACT

An intercalary prosthesis spans a space in the shaft of a long bone between native proximal and distal ends of the long bone. The intercalary prosthesis has first and second intercalary segments connected to proximal and distal stem components. The stem components are implanted in the proximal and distal ends of the long bone. One of the intercalary segments has a male dovetail and the other has a female dovetail. The male and female dovetails are positioned to allow the male dovetail to be moved into the female dovetail in a direction other than the proximal-distal direction. The intercalary segments can thus be connected after the segments have been implanted without damaging the soft tissue at the native bone through distraction. The intercalary segments and stem components are provided as part of a kit. The method of implanting the intercalary prosthesis is also disclosed.

9 Claims, 8 Drawing Sheets

U.S. PATENT DOCUMENTS

| | | | |
|---|---|---|---|
| 5,011,496 A | 4/1991 | Forte | |
| 5,072,070 A | 12/1991 | Balsells | |
| 5,079,388 A | 1/1992 | Balsells | |
| 5,082,390 A | 1/1992 | Balsells | |
| 5,100,407 A | 3/1992 | Conrad | |
| 5,108,078 A | 4/1992 | Balsells | |
| 5,108,437 A | 4/1992 | Kenna | |
| 5,117,066 A | 5/1992 | Balsells | |
| 5,139,276 A | 8/1992 | Balsells | |
| 5,314,479 A | 5/1994 | Rockwood | |
| 5,334,184 A * | 8/1994 | Bimman | 606/63 |
| 5,352,227 A * | 10/1994 | O'Hara | 606/63 |
| 5,358,524 A * | 10/1994 | Richelsoph | 623/23.47 |
| 5,411,348 A | 5/1995 | Balsells | |
| 5,601,567 A | 2/1997 | Swajger et al. | |
| 6,197,065 B1 * | 3/2001 | Martin et al. | 623/23.17 |
| 6,290,725 B1 | 9/2001 | Weiss | |
| 6,357,194 B1 * | 3/2002 | Jones, Jr. | 52/590.1 |
| 6,364,909 B1 * | 4/2002 | McGee | 623/16.11 |
| 6,443,954 B1 | 9/2002 | Bramlet et al. | |
| 6,447,549 B1 | 9/2002 | Taft | |
| 6,454,810 B1 * | 9/2002 | Lob | 623/23.47 |
| 6,613,092 B1 | 9/2003 | Kana et al. | |
| 6,648,889 B1 | 11/2003 | Bramlet et al. | |
| 6,712,855 B1 * | 3/2004 | Martin et al. | 623/20.34 |
| 6,712,858 B1 | 3/2004 | Grundei et al. | |
| 6,790,234 B1 | 9/2004 | Frankle | |
| 2001/0041941 A1 | 11/2001 | Boyer, et al. | |
| 2003/0149486 A1 * | 8/2003 | Huebner | 623/19.11 |
| 2003/0204262 A1 | 10/2003 | Ferguson et al. | |
| 2003/0204267 A1 | 10/2003 | Hazebrouck, et al. | |
| 2004/0193266 A1 | 9/2004 | Meyer | |
| 2004/0193267 A1 * | 9/2004 | Jones et al. | 623/16.11 |
| 2004/0236339 A1 | 11/2004 | Pepper | |
| 2005/0107883 A1 | 5/2005 | Goodfried, et al. | |

FOREIGN PATENT DOCUMENTS

| | | |
|---|---|---|
| DE | 3903438 A | 8/1990 |
| DE | 19633865 A | 2/1998 |
| DE | 19722389 A | 12/1998 |
| DE | 19722389 A1 * | 12/1998 |
| EP | 212192 A1 | 3/1987 |
| EP | 1234557 A | 8/2002 |
| EP | 1358860 A | 11/2003 |
| FR | 2633509 A | 1/1990 |
| WO | WO 02/05732 A | 1/2002 |

OTHER PUBLICATIONS

Centerpulse Orthopedics, Inc. web site page: MOST Options ™; *Modular Knee and Hip Otpions for Severe Bone Loss and Trauma*; http://www.centerpulseorthopedics.com/most_options/knee/index. (2 pages).

Wright Medical Technology, Inc,: Guardian™ Limb Salvage System: Surgical Technique brochure: *Total Femoral Replacement*. 2001, Wright Medical Technology, Inc. (19 pages).

Wright Medical Technology, Inc.,: Guardian™ Limb Salvage System: Surgical Technique brochure: *Distal Femoral Replacement* 2001, Wright Medical Technology, Inc. (19 pages).

Wright Medical Technology, Inc., Guardian™ Limb Salvage System: Surgical Technique brochure: *Proximal Femoral Replacement*. 2001, Wright Medical Technology, Inc. (11 pages).

Biomet®, Inc. website: Finn® *Salvage/oncology System*; http://www.biomet.com/knees/finn.cfm 2001, 2002. (Form No. Y-BMT-698/123100/M) (2 pages).

Howmedica Osteonics Corp. web site: Product Overview: *Modular-Replacement System*: http://www.howost.com/kneesystems/mrs/text.php: http://www.howost.com/kneesystems/mrs/overview.htm: http://www.howost.com/kneesystems/mrs/proxtemur.htm: http://www.howost.com/kneesystems/mrs/distalfemur.htm: http://www.howost.com/kneesystems/mrs/totalfemurr.htm: http://www.howost.com/kneesystems/mrs/proxtibiar.htm: http://www.howost.com/kneesystems/mrs/shoulderrhtm. 1997, Howmedica Osteonics Corp. (7 pages).

Biomet®, Inc. *Knee System Modularity and Surgical Latitude* brochure. 1995. (Form No. Y-BMT-382/021095/H) (22 pages).

Biomet®, Inc. *Proximal Humeral Replacement™ System* brochure 1996. (Form No. Y-BMT-466/043096/H) (2 pages).

Biomet®, Inc. *Finn™ Knee System Product Release Overview* brochure, including pp. 1-30.

Biomet®, Inc. *The Finn Knee: Rotating Hinge Replacement of the Knee Preliminary Report of New Design* document, pp. 413-416.

Howmedica Osteonics Corp. Modular Replacement System: *A Simple, Comprehensive, Modular System for Radical Bone Resections of Proximal Femur, Distal Femur, Total Femur, Proximal Tibia, Proximal Humerus* brochure. 1997 Howmedica, inc. (7100-0-001 -0 5M Sep. 1997 5807 TG/HAR). (6 pages).

Stryker Howmedica Osteonics Corp: *Modular Rotating Hinge Knee System* brochure. 2000 Stryker COrporation (6481-2-085 LI Jun. 2000). (4 pages).

Howmedica International: *Howmedica Modular Resection System* brochure (XXK/01/0391/4E). (12 pages).

Sulzer Medica: *Sulzer™ Orthopedics MOST™ System* brochure (1000-01-607) (Oct. 1997 1.5M 1997 Sulzer Orthopedics, Inc. (2 pages).

Wright Medical Technology, Inc.: Segmental Oncology System—*The S.O.S. Proximal Femur* brochure (4 pages).

Wright Medical Technology, Inc.: Segmental Orthopedic System—*The Salvage Solution—The S.O.S. Proximal Femur* brochure (7 pages).

BALSEAL ENGINEERING, Canted Coil Springs web page: Aug. 21, 2002.

Stryker Howmedica Osteonics: *Modular Replacement System: Distal Femoral Resection for Large Segmental Replacements—Surgical Technique* Brochure.

European Search Report EP 0359485A dated Mar. 21, 1990, for corresponding EP Application No. 05255808.

International Search Report dated May 11, 2006, regarding PCT Application No. PCT/US05/45197.

* cited by examiner

INTERCALARY PROSTHESIS, KIT AND METHOD

FIELD OF THE INVENTION

The present invention relates to prosthetic systems for replacement of parts of bones, and more particularly to prosthetic systems for replacement of mid-shaft parts of bones.

BACKGROUND OF THE INVENTION

Severe trauma and disease can lead to significant amounts of bone loss. In some instances, it is necessary to excise intercalary bone from a long bone, that is, part of the diaphysis or bone shaft between the ends of the long bone, but it is not necessary to excise the ends of the long bone. Thus, for example, a portion of the shaft of the femur may need to be excised to remove a malignancy, while the ends of the femur defining parts of the hip and knee joint may be healthy. Similarly, it may be necessary to excise part of the shaft of the tibia or humerus while the ends of these bones are healthy. Rather than remove the healthy ends of the bone, it may be desirable to leave the healthy portions of the bone in place and remove the damaged or diseased bone. In these circumstances, the empty span between the ends of the bone must be replaced with some type of mid-shaft prosthesis that spans the distance between the native bone ends. The mid-shaft prosthesis can include stems that fit into the intramedullary canals of the native bone ends and a body that extends between these stems. However, it may be difficult to implant such a mid-shaft prosthesis. Implantation can require that the native bone ends be distracted proximally and distally in order to fit the mid-shaft prosthesis into position. Since the native bone ends are surrounded by and connected to soft tissue, distraction of the native bone ends can damage the soft tissue and the connections between the soft tissue and the native bone ends.

SUMMARY OF THE INVENTION

The present invention addresses the need for intercalary prosthetics that can be used to replace portions of the diaphyseal parts of the long bone that have been removed or excised. The present invention addresses this need while also addressing the need for such prosthetics that can be implanted and affixed to the remaining parts of the native bone while minimizing damage to soft tissue at the ends of the native bone.

In one aspect, the present invention provides an intercalary prosthesis to span a space in the shaft of a long bone between native proximal and distal ends of the long bone. The prosthesis comprises first and second intercalary segments. The first intercalary segment is secured to one bone portion and the second intercalary segment is secured to another bone portion. One of the intercalary segments has a male portion and the other of the intercalary segments has a female portion. The male portion is received in the female portion to connect the first and second intercalary segments together. The male and female portions are shaped and positioned to allow the male portion to be moved into the female portion in a direction other than the proximal-distal direction.

In another aspect, the present invention provides a surgical kit for creating an intercalary prosthesis to span a space in the shaft of a long bone between native proximal and distal ends of the long bone. The kit comprises a first intercalary segment having a male portion and a second intercalary segment having a female portion. The male and female portions of the first and second intercalary segments are shaped and positioned to allow the male portion of the first intercalary segment to be moved into the female portion of the second intercalary segment to connect the first and second intercalary segments after the first and second intercalary segments have been secured to native bone without proximal-distal distraction of the native bone.

In another aspect, the present invention provides a method of surgically replacing a missing part of the shaft of a long bone. The method comprises preparing the long bone so that proximal and distal portions of the long bone remain. An intercalary prosthesis having a proximal part and a distal part is provided. The proximal part of the intercalary prosthesis is implanted in the proximal part of the bone and the distal part of the intercalary prosthesis is implanted in the distal part of the bone. The proximal and distal parts of the intercalary prosthesis are connected after implantation without distracting the proximal and distal parts of the bone in the proximal-distal direction.

Additional features of the present invention will become apparent to those skilled in the art upon consideration of the following detailed description of preferred embodiments exemplifying the best mode of carrying out the invention as presently perceived.

DETAILED DESCRIPTION

Figure 1:
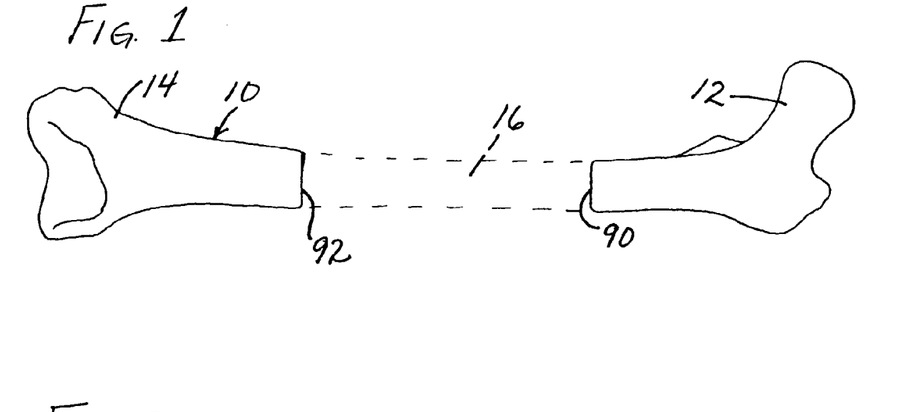
FIG. 1 is a top plan or anterior view of a femur, showing the native proximal and distal ends of the femur and showing an excised intercalary segment of the diaphysis of the femur in phantom between the native ends of the femur.

FIG. 1 illustrates a long bone, and in particular, a femur 10 with proximal and distal ends 12, 14. The proximal end 12 of the femur 10 comprises the femoral head and adjacent bone tissue; the distal end 14 of the femur comprises the femoral condyles and adjacent bone tissue. FIG. 1 also illustrates in phantom the intercalary segment 16 of diaphyseal bone that has been removed, due to, for example, disease or severe trauma. Although the present invention is illustrated in use with the femur, it should be understood that the invention is not so limited; the invention could be used in any other long bone, such as the tibia or humerus, where a portion of the shaft has been removed or is missing.

Figure 2:
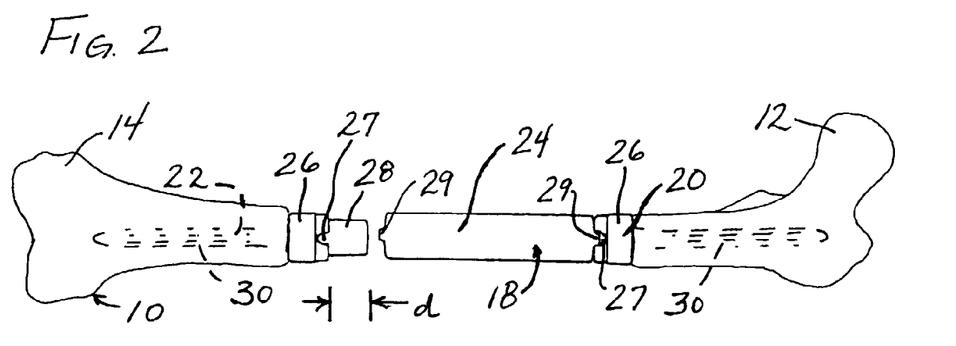
FIG. 2 is a top plan or anterior view of the femur of FIG. 1, shown with one type of intercalary prosthesis prior to connection of all the parts of the intercalary prosthesis.
Figure 3:
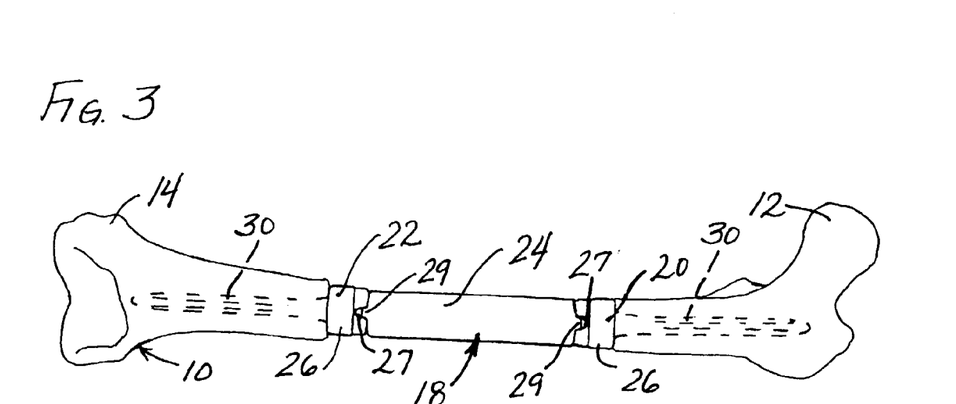
FIG. 3 is a top plan or anterior view of the femur of FIGS. 1–2, shown with all parts of the intercalary prosthesis connected together.

FIG. 2 illustrates the femur 10 of FIG. 1 in an intraoperative state, with a modular mid-shaft prosthesis 18. FIG. 3 illustrates the femur of FIGS. 1–2 at the end of the surgical procedure. The mid-shaft prosthesis 18 of FIG. 2 is that disclosed in U.S. patent application Ser. No. 10/135,791 filed on Apr. 30, 2002 and entitled "Modular Limb Preservation System," and is shown at FIGS. 5 and 9. That patent application is incorporated by reference herein in its entirety.

The mid-shaft prosthesis 18 illustrated in FIGS. 2–3 comprises a proximal stem component 20, a distal stem component 22 and a spacer component 24. Each of the stem components 20, 22 includes a head portion 26 from which extends a male connection element Morse taper post 28. The head portion 26 also includes a pair of notches 27 that receive tabs 29 on the spacer component 24. Each of the stem components 20, 22 also includes a stem portion 30 that is shaped to receive in the intramedullary canal of the bone.

As shown in FIG. 2, to implant the mid-shaft prosthesis 18 in the bone 10, the two stem components 20, 22 may be implanted in the intramedullary canals of the two spaced ends 12, 14 of the bone 10. The spacer component 24 can be connected to one of the stem portions 20, 22 before the stem portion is implanted, or could also be connected after the stem portion is implanted. To complete the assembly, the native proximal and distal ends 12, 14 of the bone 10 with the proximal and distal stem components 20, 22 and spacer component 24 must be distracted, or moved in the proximal-distal direction, by at least a distance "d" (shown in FIG. 2), corresponding with the length of the Morse taper post 28 so that the Morse taper post 28 can be inserted into the mating female portion of the spacer component 24. In the illustrated embodiment, the dimension "d" is typically on the order of 20 mm. This degree of proximal-distal distraction of the native bone ends 12, 14 could damage the surrounding soft tissue and soft tissue that is connected to the native bone ends 12, 14.

To avert the potential for soft tissue damage, the present invention obviates the need for proximal-distal distraction of the native bone ends 12, 14 while retaining the advantages of the system disclosed in U.S. patent application Ser. No. 10/135,791. In the present invention, the two stem portions 20, 22 can be connected to an intervening two-part spacer component without undue distraction of the native proximal and distal end bone portions 12, 14.

Figure 4:
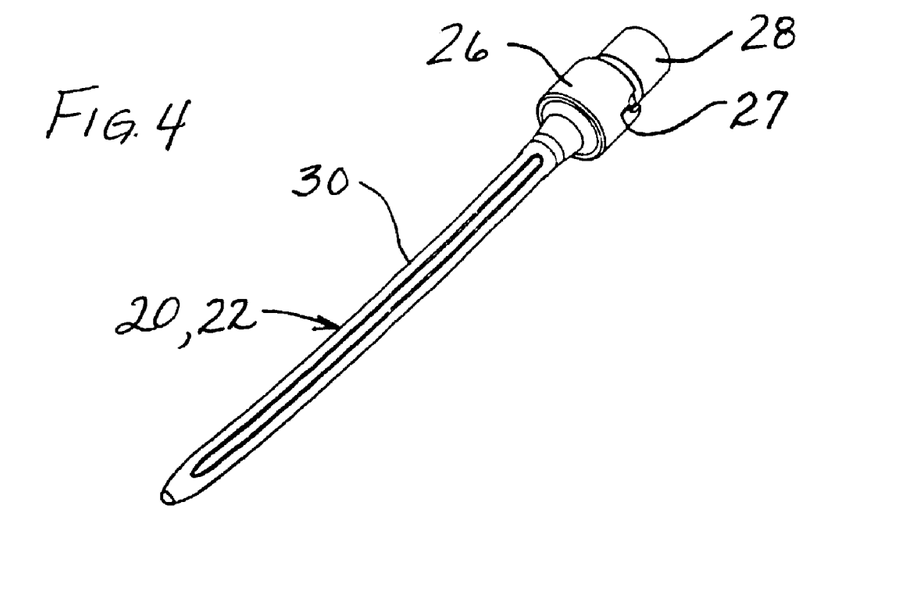
FIG. 4 is a perspective view of one embodiment of a stem component for engagement within the intramedullary canal of an end portion of a long bone for use as part of the intercalary prosthesis of the present invention.
Figure 5:
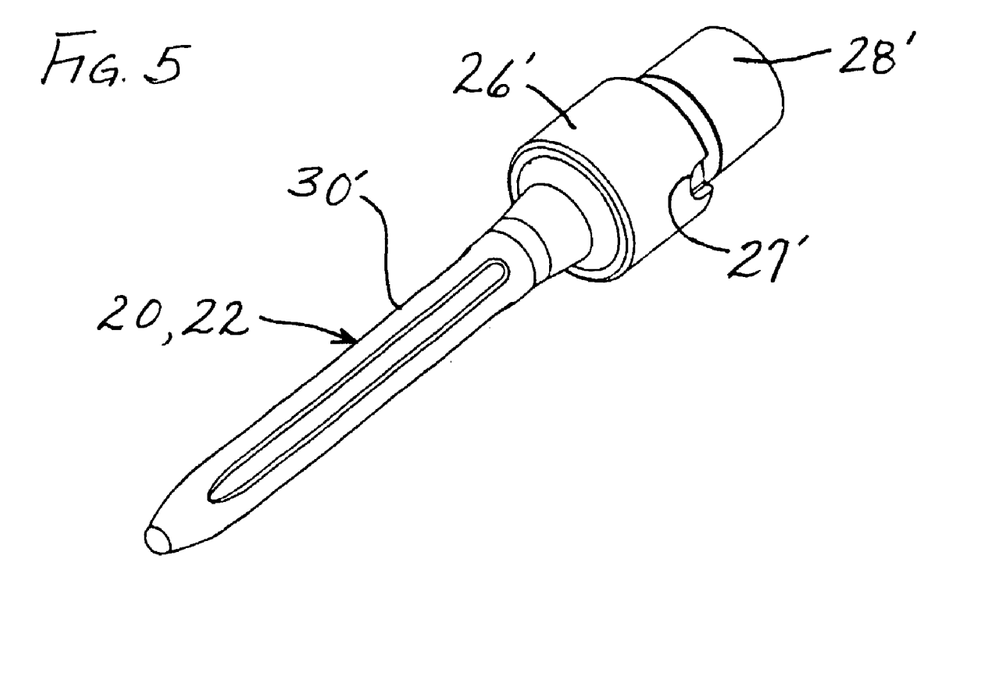
FIG. 5 is a perspective view of another embodiment of a stem component for engagement within the intramedullary canal of an end portion of a long bone for use as part of the intercalary prosthesis of the present invention.
Figure 6:
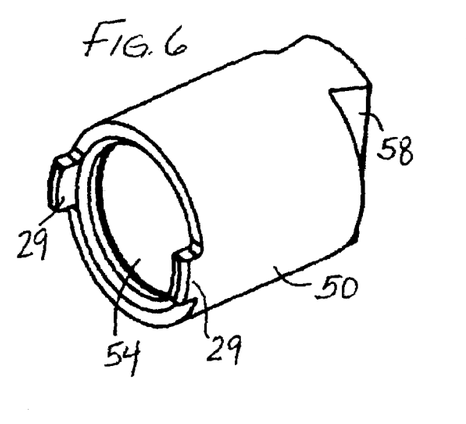
FIG. 6 is a perspective view of one embodiment of a first intercalary segment for use as part of the intercalary prosthesis of the present invention.
Figure 7:
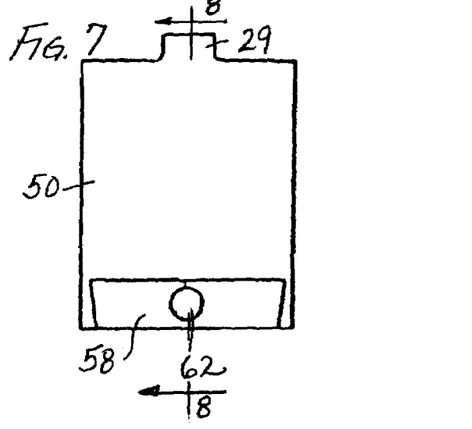
FIG. 7 is an elevation of the first intercalary segment of FIG. 6.
Figure 28:
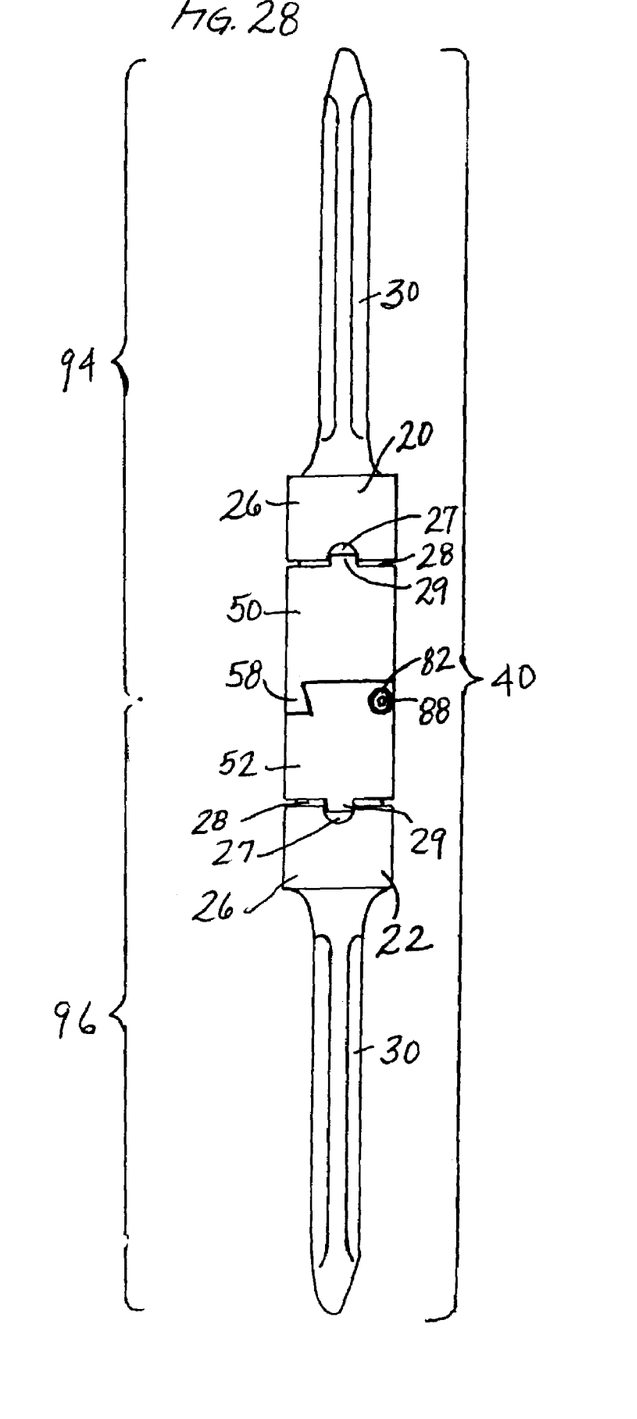
FIG. 28 is a top plan view of an intercalary prosthesis according to the present invention.

The mid-shaft or intercalary prosthesis of the present invention comprises an assembly identified at 40 in FIG. 28. The mid-shaft or intercalary prosthesis 40 comprises proximal and distal stem components like those described in U.S. patent application Ser. No. 10/135,791. A surgical kit including the intercalary prosthesis 40 of the present invention could include stem components 20, 22 like those shown in FIGS. 4–5 with stems 30, 30' of different lengths or other different characteristics. Generally, all of the stem components 20, 22 would have head portions 26, 26' of the same size and shape to allow the stem components to be used interchangeably in the system described in U.S. patent application Ser. No. 10/135,791. Thus, the Morse taper posts 28, 28' would be the same dimensions and shapes so that they can be received in all of the female parts of the system.

Figure 27:
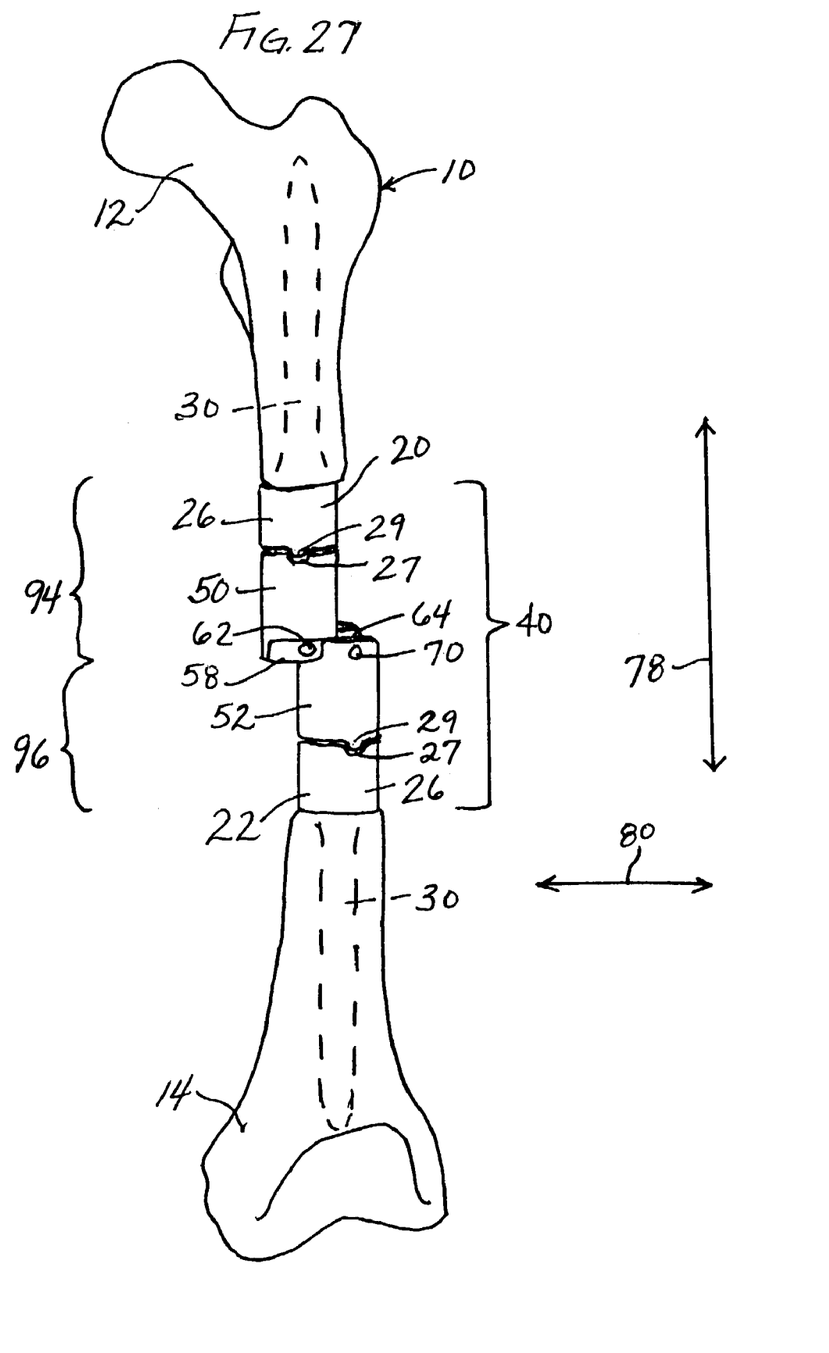
FIG. 27 is a top plan or anterior view of two end portions of a femur with sub-assemblies according to the present invention implanted in the end portions, illustrating connecting the two sub-assemblies.

In the present invention, the spacer component comprises at least two connected intercalary segments. An example of a spacer component comprising two connected segments 50, 52 is shown in FIGS. 27 and 28.

Both the first intercalary segment 50 and the second intercalary segment 52 have open female ends with Morse taper bores 54. Each Morse taper bore 54 can receive and mate with the Morse taper post 28 of one of the stem components 20, 22. Each Morse taper bore 54 can also receive and mate with a Morse taper post 28 of one of male ends of one of the other system components described in U.S. patent application Ser. No. 10/135,791. The length of the Morse taper post 28 of each stem component 20, 22 is calibrated to the depth of the Morse taper bore 54 so that any component of the system having a Morse taper post can mate with the first intercalary element 50.

Both the first intercalary segment 50 and the second intercalary segment 52 have diametrically opposed tabs 29 like those described in U.S. patent application Ser. No. 10/135,791. Each tab 29 can be received in one of the notches 27 of the one of the stem components 20, 22.

As shown in FIGS. 8–10, 14–16, 19–21 and 24–26, both the first intercalary segment 50 and the second intercalary segment 52 also have pressure relief bores 56 at the end walls defining the Morse taper bores 54 so that air pressure can be relieved as the Morse taper elements 28, 54 are brought together.

Figure 8:
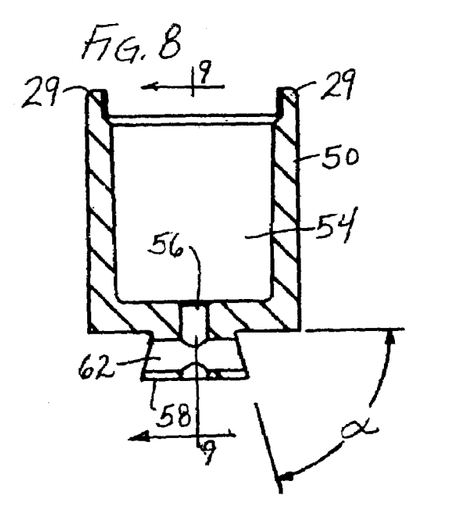
FIG. 8 is a cross-section of the first intercalary segment of FIGS. 6–7, taken along line 8—8 of FIG. 7.
Figure 9:
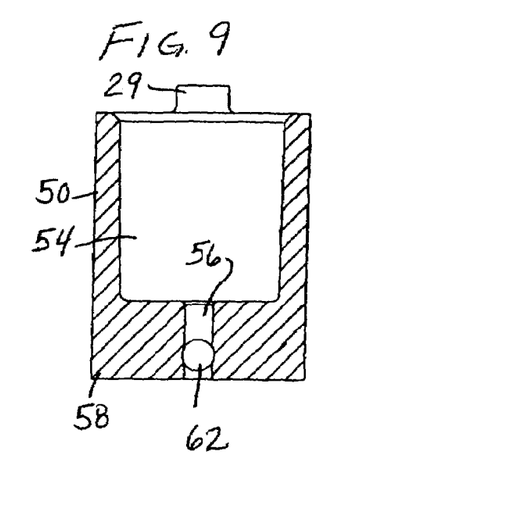
FIG. 9 is a cross-section of the first intercalary segment of FIGS. 6–8, taken along line 9—9 of FIG. 8.
Figure 10:
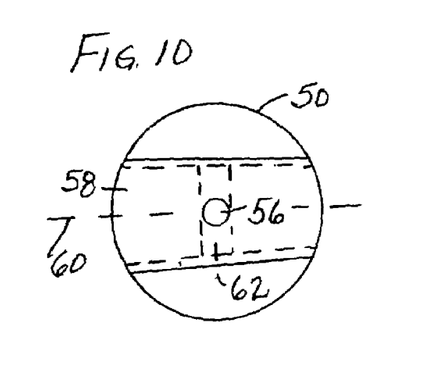
FIG. 10 is a bottom plan view of the first intercalary segment of FIGS. 6–9.

As shown in FIGS. 6–10, the first intercalary segment 50 includes a transverse male dovetail 58 at the end opposite the opening into the Morse taper bore 54. As shown in FIG. 8, the male dovetail 58 flares outwardly at an angle α so that it is widest at its free end. In the illustrated embodiment, the angle α is about 75°. As shown in the bottom plan view of FIG. 10, the male dovetail 58 is symmetrical about a diameter 60, and also tapers toward the diametrical line of symmetry 60 from a greatest dimension along one side to a smallest dimension opposite the greatest dimension.

In the embodiment shown in FIGS. 6–10, the first intercalary segment also includes a smooth through-bore 62 in the male dovetail 58. The through-bore 62 is generally perpendicular to the diametrical line of symmetry 60 of the male dovetail 58.

Figure 14:
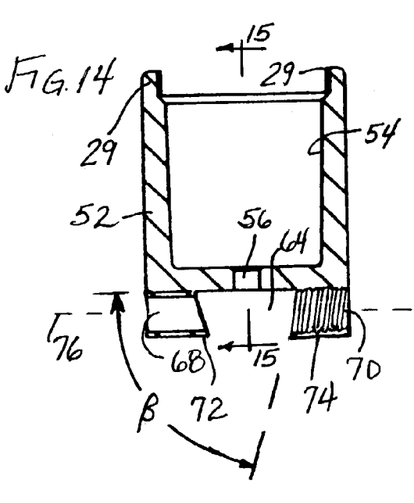
FIG. 14 is a cross-section of the second intercalary segment of FIGS. 12–13, taken along line 14—14 of FIG. 13.
Figure 15:
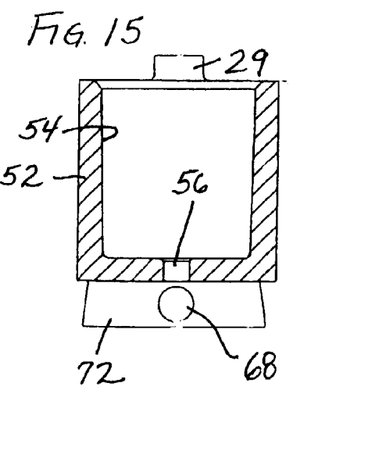
FIG. 15 is a cross-section of the second intercalary segment of FIGS. 12–14, taken along line 15—15 of FIG. 14.
Figure 16:
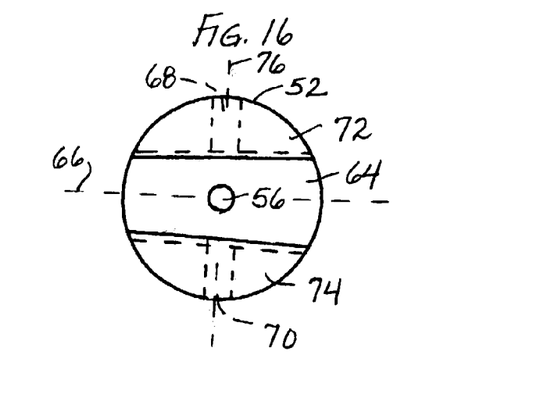
FIG. 16 is a bottom plan view of the second intercalary segment of FIGS. 12–15.
Figure 17:
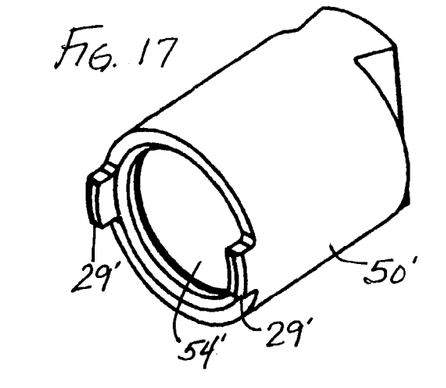
FIG. 17 is a perspective view of a second embodiment of a first intercalary segment for use as part of the intercalary prosthesis of the present invention.
Figure 18:
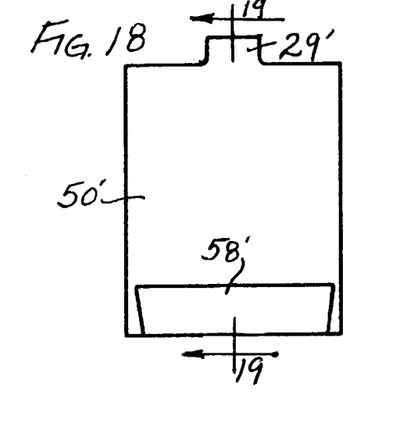
FIG. 18 is an elevation of the first intercalary segment of FIG. 17.
Figure 19:
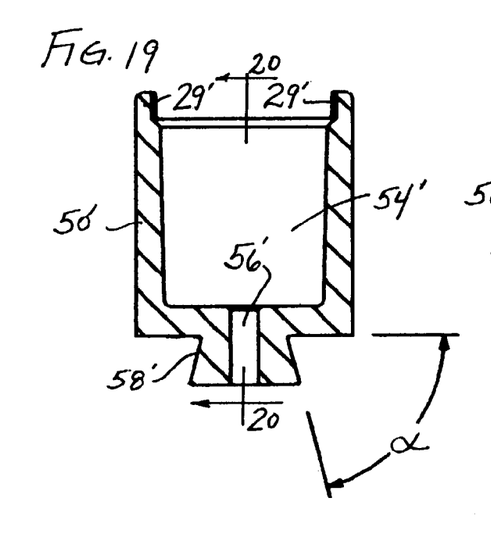
FIG. 19 is a cross-section of the first intercalary segment of FIGS. 17–18, taken along line 19—19 of FIG. 18.
Figure 20:
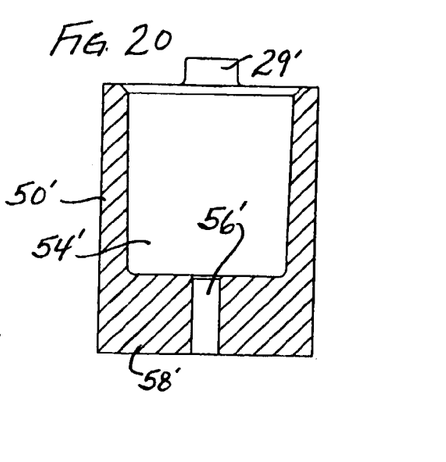
FIG. 20 is a cross-section of the first intercalary segment of FIGS. 17–19, taken along line 20—20 of FIG. 19.
Figure 21:
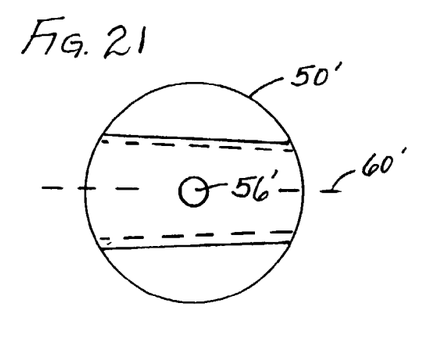
FIG. 21 is a bottom plan view of the second intercalary segment of FIGS. 17–20.
Figure 22:
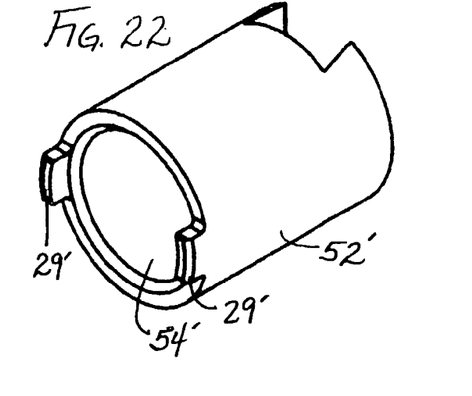
FIG. 22 is a is a perspective view of a second embodiment of a second intercalary segment for use as part of the intercalary prosthesis of the present invention.
Figure 23:
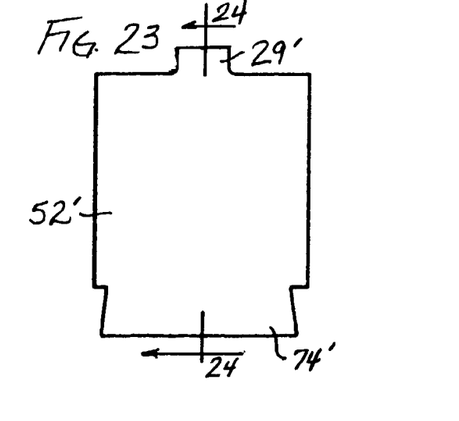
FIG. 23 is an elevation of the second intercalary segment of FIG. 22.
Figure 24:
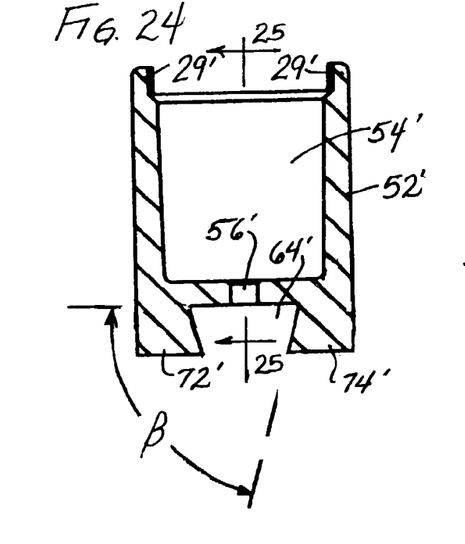
FIG. 24 is a cross-section of the second intercalary segment of FIGS. 22–23, taken along line 24—24 of FIG. 23.
Figure 25:
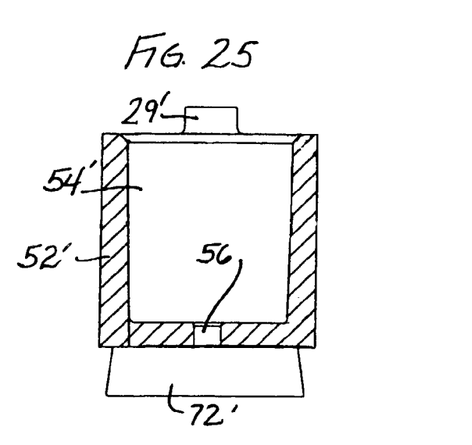
FIG. 25 is a cross-section of the second intercalary segment of FIGS. 22–24, taken along line 25—25 of FIG. 24.
Figure 26:
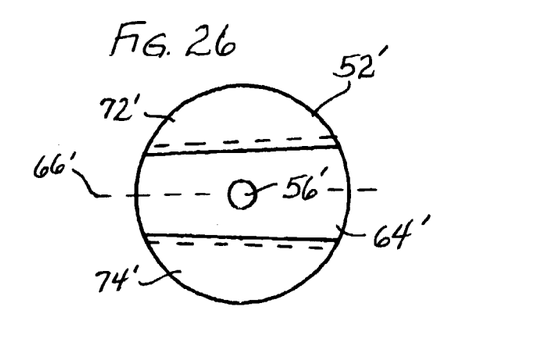
FIG. 26 is a bottom plan view of the second intercalary segment of FIGS. 22–25.

As shown in FIGS. 12–16, the second intercalary segment 52 includes a transverse female dovetail 64 at the end opposite the Morse taper bore 54. As shown in FIG. 14, the female dovetail 64 tapers inwardly at an angle β. In the illustrated embodiment, the angle β is about 75°. As shown in the bottom plan view of FIG. 16, the female dovetail 64 is symmetrical about a diameter 66, tapering toward the diametrical line of symmetry 66 from a greatest dimension along one side to a smallest dimension along the opposite side.

In the embodiment illustrated in FIGS. 12–16, the second intercalary segment 52 includes two bores 68, 70 in the body portions 72, 74 defining the female dovetail 64. The bores 68, 70 are generally perpendicular to the diametrical line of symmetry 66 of the female dovetail 64. One of the bores 68 is smooth and the other bore 70 is threaded. The bores 68, 70 are coaxial, and their axis 76 intersects the female dovetail 64.

The male dovetail 58 and female dovetail 64 are sized and shaped so that the first and second intercalary segments 50, 52 can be connected together at the dovetails 58, 64 by sliding the male dovetail 58 into the female dovetail 64 as shown in FIG. 27. As there shown, the two intercalary segments 50, 52 can be connected without moving the segments and bone portions 12, 14 in a proximal-distal direction, shown at 78 in FIG. 27. Instead, the intercalary segments 50, 52 can be connected by moving one or both of the segments 50, 52 in a direction other than the proximal-distal direction 78, such as in a generally medial-lateral direction 80 as shown in FIG. 27 or in an anterior-posterior direction. By so connecting the two intercalary segments 50, 52, the mid-shaft prosthesis 18 can be assembled intraoperatively after the stem components 20, 22 have been implanted without substantial distraction of the native bone portions 12, 14.

Figure 11:
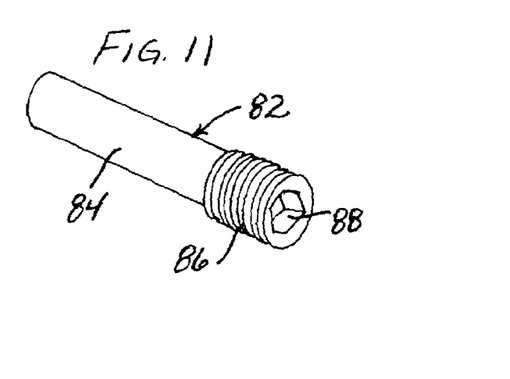
FIG. 11 is a perspective view of a dowel pin for use with the first embodiment of the first and second intercalary segments.
Figure 12:
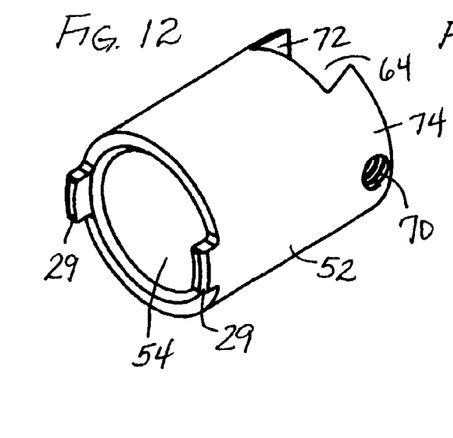
FIG. 12 is a perspective view of one embodiment of a second intercalary segment for use as part of the intercalary prosthesis of the present invention.
Figure 13:
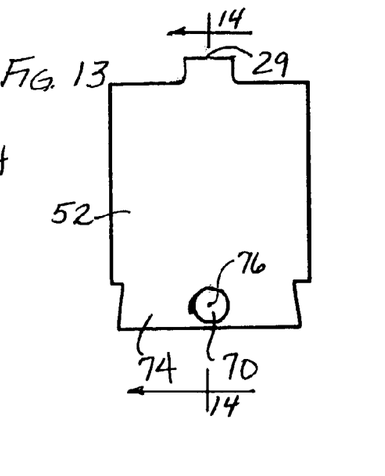
FIG. 13 is an elevation of the second intercalary segment of FIG. 12.

In the embodiment of FIGS. 6–16 and 27–28, when the male and female dovetails 58, 64 of the two intercalary segments 50, 52 have been slid together into their mating relationship, the through bore 62 of the male dovetail 58 is aligned co-axially with the bores 68, 70 of the intersecting the body portions 72, 74 of the second intercalary segment 52. To secure the intercalary segments 50, 52 together, the first embodiment of the invention also includes a dowel pin 82 shown in FIG. 11. The dowel pin 82 has a portion 84 with a smooth cylindrical outer surface and an end portion 86 that has external threads and an internal opening 88 shaped to be capable of receiving the end of a tool (not shown) for rotating the dowel pin 82. The dowel pin 82 is sized so that its smooth cylindrical portion 84 can be received in the through bore 62 of the male dovetail 58 and the smooth bore 68 adjacent the female dovetail 64 and so that the dowel pin's threaded portion 86 can be received within and engage the threaded bore 70 adjacent the female dovetail 64. Once the dowel pin 82 is positioned, as shown in FIG. 28, relative movement between the first and second intercalary segments 50, 52 is limited or eliminated.

It should be understood that structures other than a dowel pin 82 can be used as a retaining member to limit relative movement between the first and second intercalary segments. For example, a pin with a spring connection could be used.

Alternative embodiments for the first and second intercalary segments are illustrated in FIGS. 17–26. These segments and their features are illustrated with reference numbers like those used for the first embodiment, with a prime symbol. In the embodiments of FIGS. 17–26, the male and female dovetails 58', 64' are sized and shaped to frictionally lock when assembled; no bores or dowel pin are used in this embodiment.

The illustrated segments 50, 52, 50', 52', the dowel pin 82 and the stem components 20, 22 may be made of medical grade materials standard for prosthetic implants. For example, standard titanium alloys and cobalt-chrome alloys can be used for these parts. In addition, portions of the segments 50, 52, 50', 52' and the stem components 20, 22 can be provided with porous surfaces if desired.

The illustrated segments, dowel pin 82 and stem components 20, 22 can be provided as parts of a surgical kit. The kit can include different sizes of these parts, such as stem components 20, 22 with different lengths of stems 30. The kit can also include, for example, a distal femoral component (not shown), a proximal femoral component (not shown) and tibial components (not shown) of various sizes. The kit can also include additional segmental components of the type described and shown in U.S. patent application Ser. No. 10/135,791; a plurality of such segmental components of different lengths can be included in the kit.

For maximum versatility with minimal costs, a surgical kit utilizing the teachings of the present invention could include the intercalary segmental components 50, 52 or 50', 52' of one length along with other segmental components of various lengths to accommodate the need for different spans of bone loss and different lengths of bone. Thus, the intercalary segmental components of the present invention could be provided as parts of the kits described in U.S. patent application Ser. No. 10/135,791. Alternatively, multiple lengths of either one or both of the intercalary segments 50, 52 or 50', 52' could be included in a surgical kit.

To use the intercalary segmental components of the present invention, the surgeon can prepare the long bone (e.g. the femur, tibia, humerus, etc.) to remove the diseased portion of the diaphyses or to remove bone fragments produced by some injury. The surgeon can then ream the intramedullary canals of the healthy proximal and distal bone portions 12, 14 in a standard manner to receive the stems of the stem components. The inner ends 90, 92 (see FIG. 1) of the native bone portions 12, 14 can be resected to provide a generally flat surface against which the intercalary implant components can seat.

The surgeon can use the trial components described and illustrated in U.S. patent application Ser. No. 10/135610 entitled "Quick Disconnect Orthopaedic Trials", filed on Apr. 30, 2002, which is incorporated by reference herein in its entirety. Once the surgeon has determined the appropriate sizes for the implant components from the trial, the surgeon can assemble the proximal and distal ends of the intercalary implant.

The surgeon can assemble one stem component 20 with the first intercalary segment 50 by inserting the Morse taper post 28 of the stem component into the Morse taper bore 54 of the intercalary segment 50 until the appropriate frictional lock is created between the two components 20, 50, creating a proximal sub-assembly shown at 94 in FIGS. 27–28. The surgeon can then assemble the other stem component 22 with the second intercalary segment 52 by inserting the Morse taper post 28 of the stem component 22 into the Morse taper bore 54 of the second intercalary segment 52, creating a distal sub-assembly shown at 96 in FIGS. 27–28. Each sub-assembly 94, 96 can then be implanted in the prepared intramedullary canal of the respective native bone portion 12, 14.

Once both sub-assemblies 94, 96 have been implanted, the two sub-assemblies 94, 96 can be connected as shown in FIG. 27 to create the intercalary prosthesis 40. The adjacent ends of the sub-assemblies 94, 96 can be moved slightly in a generally medial-lateral direction (or anterior-posterior direction) and the male dovetail 58 can then be inserted into the female dovetail 64. No proximal-distal distraction is necessary. The intercalary segments 50, 52 can then be brought together until the male dovetail 58 is fully received in the female dovetail 64. If the segments 50, 52 are designed to frictionally lock, then no further securing is necessary. If the segments 50, 52 are designed to accept a dowel pin 82, the pin can then be inserted to lock the segments 50, 52 together. The surgeon can then complete the surgery in the standard manner.

It should be understood that the above-described surgical technique is provided by way of example only, and that the present invention is not limited to that technique unless expressly called for in the claims. Variations are possible; for example, the surgeon could opt to connect the intercalary segments 50, 52 and the stem components 20, 22 after the stem components have been implanted in the native bone portions 12, 14.

It should also be understood that the mating male and female dovetails 58, 64 are provided as examples of mechanical connections that do not require proximal and distal movement of the native bone portions 12, 14. Other types of connections that provide a stable connection could be used. In addition, some limited amount of proximal-distal distraction of the native bone portions 12, 14, could be acceptable if the native soft tissue is not damaged by the process. Unless expressly called for in the claims, the invention is not limited to use of male and female dovetails and is not limited to any particular degree of proximal-distal distraction.

An alternative design for an intercalary prosthesis is described and illustrated in an application for United States Patent filed concurrently herewith by Michael C. Jones and Natalie S. Heck and entitled "Intercalary Implant," which is incorporated by reference herein in its entirety.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

I claim:

1. An intercalary prosthesis to span a space in the shaft of a long bone between native proximal and distal ends of the long bone, the prosthesis comprising:
   a proximal stem component adapted to be received in the intramedullary canal of the proximal portion of the long bone;
   a distal stem component adapted to be received in the intramedullary canal of the distal portion of the long bone;
   a first intercalary segment including a first end, a second end and a substantially cylindrical one-piece outer surface sized and shaped to replace a portion of the shaft of the long bone;
   a second intercalary segment including a first end, a second end and a substantially cylindrical one-piece outer surface sized and shaped to replace a portion of the shaft of the long bone;
   one of the intercalary segments having a male portion at one end and the other of the intercalary segments having a female portion at one end;
   the stem components and the intercalary segments having mating posts and bores for securing the stem components to the intercalary segments;
   the female portion being capable of receiving the male portion to connect the first and second intercalary segments together, the connected first and second intercalary segments being adapted to span the space in the shaft of the long bone;
   wherein the male and female portions are shaped and positioned to allow the male portion to be moved in a direction transverse to the longitudinal axes of the first and second intercalary segments into the female portion after the first intercalary segment and proximal stem component have been secured together and to the native proximal end of the long bone and after the second intercalary segment and distal stem component have been secured together and to the native distal end of the same long bone without distracting the native proximal end and native distal end of the long bone in the proximal-distal direction.

2. The intercalary prosthesis of claim 1 wherein the proximal stem component includes a Morse taper post, the first intercalary segment includes a Morse taper bore, the distal stem component includes a Morse taper post, and the second intercalary segment includes a Morse taper bore, and wherein the male and female portions of the intercalary segments comprise mating dovetails.

3. The intercalary prosthesis of claim 1 wherein the male and female portions comprise mating dovetails.

4. The intercalary prosthesis of claim 3 wherein each of the mating dovetails is tapered in two directions.

5. The intercalary prosthesis of claim 1 further comprising a retaining pin to limit relative movement between the first and second intercalary segments, the first and second intercalary segments having through bores sized and shaped to receive the retaining pin.

6. A surgical kit for creating an intercalary prosthesis to span a space in the shaft of a single long bone between native proximal and distal ends of the long bone, the kit comprising:
   a first intercalary segment having a first end, a second end, an outer surface between the first end and second end, a longitudinal axis and a male portion extending transverse to the longitudinal axis at one end, the male portion having a transverse through-bore;

a second intercalary segment having a first end, a second end, an outer surface between the first end and second end, a longitudinal axis and a female portion extending transverse to the longitudinal axis at one end, the female portion being defined by spaced body portions, each spaced body portion having a transverse through-bore aligned with the female portion;

a retaining member;

stem components capable of connection to the first and second intercalary segments;

wherein the male and female portions of the first and second intercalary segments are shaped and positioned to allow relative transverse movement between the male portion of the first intercalary segment and the female portion of the second intercalary segment to connect the first and second intercalary segments after the first and second intercalary segments have been secured to the native proximal and distal ends of the long bone without proximal-distal distraction of the native proximal and distal ends of the long bone;

wherein the retaining member pin is sized and shaped to be received in the transverse through-bores of the first and second intercalary segments to limit relative transverse movement between the first and second intercalary and; and wherein the male and female portions of the first and second intercalary segments comprise mating dovetails and wherein the stem components and intercalary segments have mating Morse taper posts and Morse taper bores.

7. The surgical kit of claim 6 wherein the male and female portions comprise mating dovetails.

8. The surgical kit of claim 7 wherein each of the dovetails is tapered in two directions.

9. The surgical kit of claim 6 wherein the retaining member comprises a pin including a threaded portion.

* * * * *